United States Patent
Waldo, Jr. et al.

(10) Patent No.: US 7,069,928 B1
(45) Date of Patent: Jul. 4, 2006

(54) HEAT-MOISTURE EXCHANGER WITH AEROSOL BY-PASS

(76) Inventors: James V. Waldo, Jr., 3205 Grenada Way, Tampa, FL (US) 33618; Christopher D. Warner, 2440 Walnut Heights Rd., Apopka, FL (US) 32703

( * ) Notice: Subject to any disclaimer, the term of this patent is extended or adjusted under 35 U.S.C. 154(b) by 0 days.

(21) Appl. No.: 11/072,070

(22) Filed: Mar. 4, 2005

(51) Int. Cl.
*A62B 18/08* (2006.01)

(52) U.S. Cl. ............... 128/201.13; 128/204.17; 128/205.12; 128/911; 165/89

(58) Field of Classification Search ........ 128/201.13, 128/204.17, 205.12, 912, 911; 165/89, 90, 165/130, 283, 297, DIG. 109, DIG. 110
See application file for complete search history.

(56) References Cited

U.S. PATENT DOCUMENTS

| | | | |
|---|---|---|---|
| 6,550,476 B1 | 4/2003 | Ryder | |
| 6,564,799 B1 | 5/2003 | Fukunaga et al. | |
| 6,588,421 B1* | 7/2003 | Diehl et al. ............ | 128/201.13 |
| 6,792,946 B1 | 9/2004 | Waldo, Jr. et al. | |
| 2004/0123974 A1* | 7/2004 | Marler et al. | |

* cited by examiner

*Primary Examiner*—Henry Bennett
*Assistant Examiner*—Andrea M. Ragonese
(74) *Attorney, Agent, or Firm*—Larson & Larson, PA; Herbert W. Larson

(57) ABSTRACT

A first and second housing is joined together by a middle housing rotatable with respect to the first and second housing. The first and second housings have conduits passing through exterior walls and an annular ring on an inside wall together with an annular interior edge rotatably joined to first and second side rim channels of the middle housing. A heat-moisture exchanger material having an annular opening through which a tube passes is mounted within the middle housing so that in a first rotatable position air and moisture passes through the first and second housing conduits directly and in a second rotatable position must pass through the heat-moisture exchange material.

15 Claims, 5 Drawing Sheets

HEAT-MOISTURE EXCHANGER WITH AEROSOL BY-PASS

BACKGROUND OF THE INVENTION

This invention relates to a patient heat-moisture exchanger attached to a nebulizer circuit. More particularly, it refers to a heat-moisture exchanger attached to a patient ventilator circuit, which includes a metered dose inhaler, the exchanger permitting medicament to pass through the heat moisture exchanger without passing through internally mounted filters and without disconnection from the ventilator circuit.

DESCRIPTION OF THE PRIOR ART

A heat-moisture exchanger attached to a nebulization device is described in U.S. Pat. No. 6,550,476. This device has a rotatable second housing connected to a first housing. The first housing has at least two chambers enclosing an absorbent material and providing a passageway for an aerosol. The second housing encloses the nebulizer. Valves control the primary gas flow through a passageway to bypass the absorbent material. This device maintains the continuity of a closed ventilator circuit when administering an aerosolized medication to prevent interruption of ventilation to a patient. However, the device is complex and expensive to produce. A simpler device is needed to maintain the continuity of a closed ventilator circuit when administering an aerosolized medication to a patient connected to a ventilation system.

U.S. Pat. No. 6,792,946 by the present inventors described a simplified way of maintaining the continuity of a closed ventilator circuit with two separate heat-moisture exchange materials. A less expensive way of achieving the same result is desirable.

SUMMARY OF THE INVENTION

The present invention provides the same effect as provided by U.S. Pat. No. 6,792,946, but achieves that same effect with a less expensive arrangement of parts. A first and a second housing is engaged to a rotatable middle housing. A heat-moisture exchange material is mounted within the middle housing and a tube passes through an opening in the heat-moisture exchange membrane so that in a first rotatable position the tube is aligned with conduits passing through an exterior wall of the first and second housing. In a second rotatable position the heat-moisture exchange material is interposed between passageways of the conduits so that air and moisture from or to a patient must pass through the heat-moisture exchange material.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION OF THE INVENTION

Figure 1:
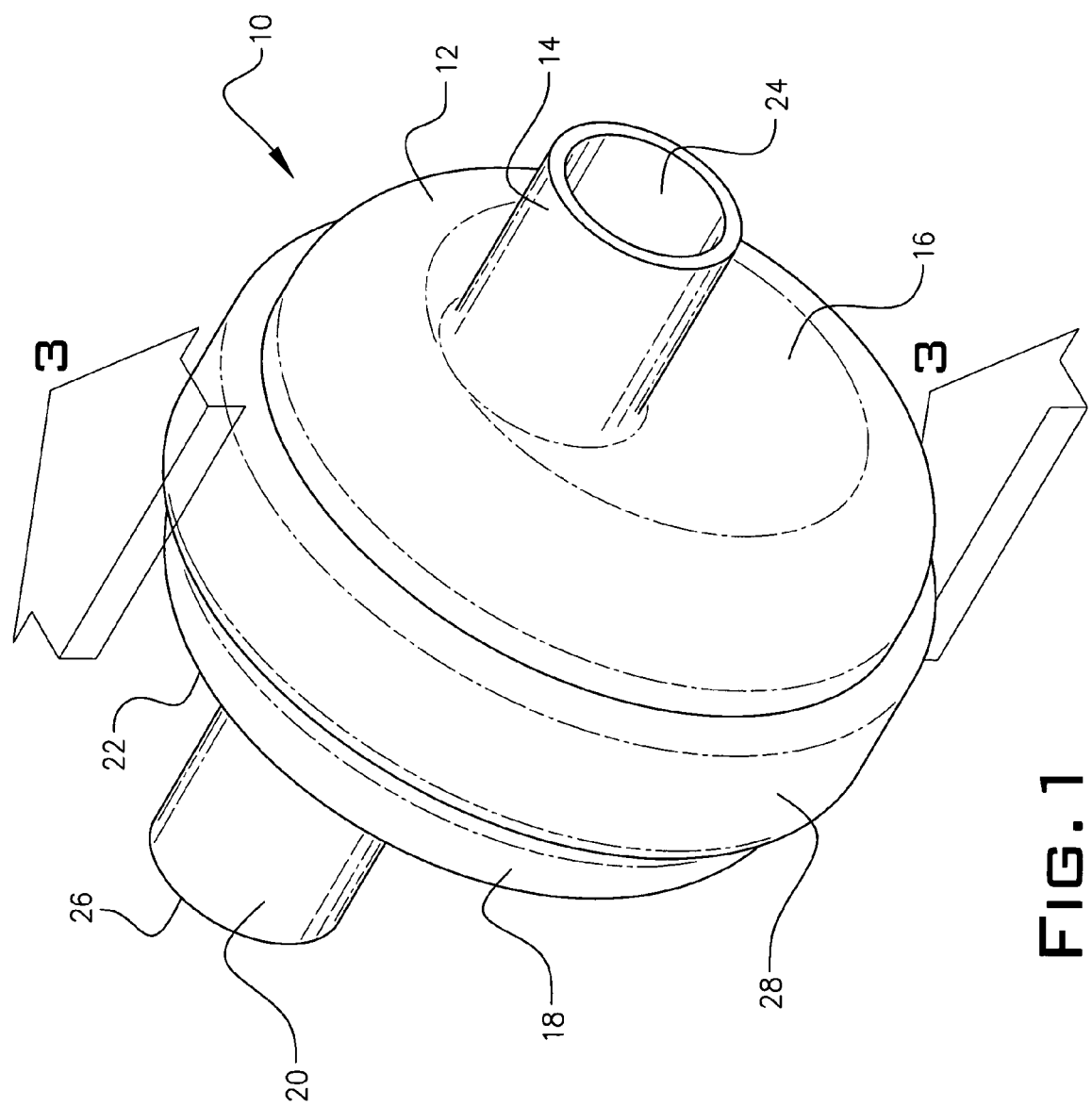
FIG. 1 is a perspective view of the heat-moisture exchange apparatus with aerosol by-pass of this invention.

Throughout the following detailed description, the same reference numerals refer to the same elements in all figures.

Referring to FIG. 1, the apparatus 10 of this invention has a first housing 12 with an integral conduit 14 passing though exterior side 16 of housing 12. Likewise, a second housing 18 has an integral conduit 20 passing though an exterior side 22. A passageway 24 in conduit 14 leads inwardly though the exterior side 22 of housing 12 and ends at groove 51. A like passageway 26 in conduit 20 leads outwardly through the exterior side 22 of housing 18 and ends at groove 57. A cylindrical rotatable middle housing 28 is interposed between the first and second housing.

Figure 2:
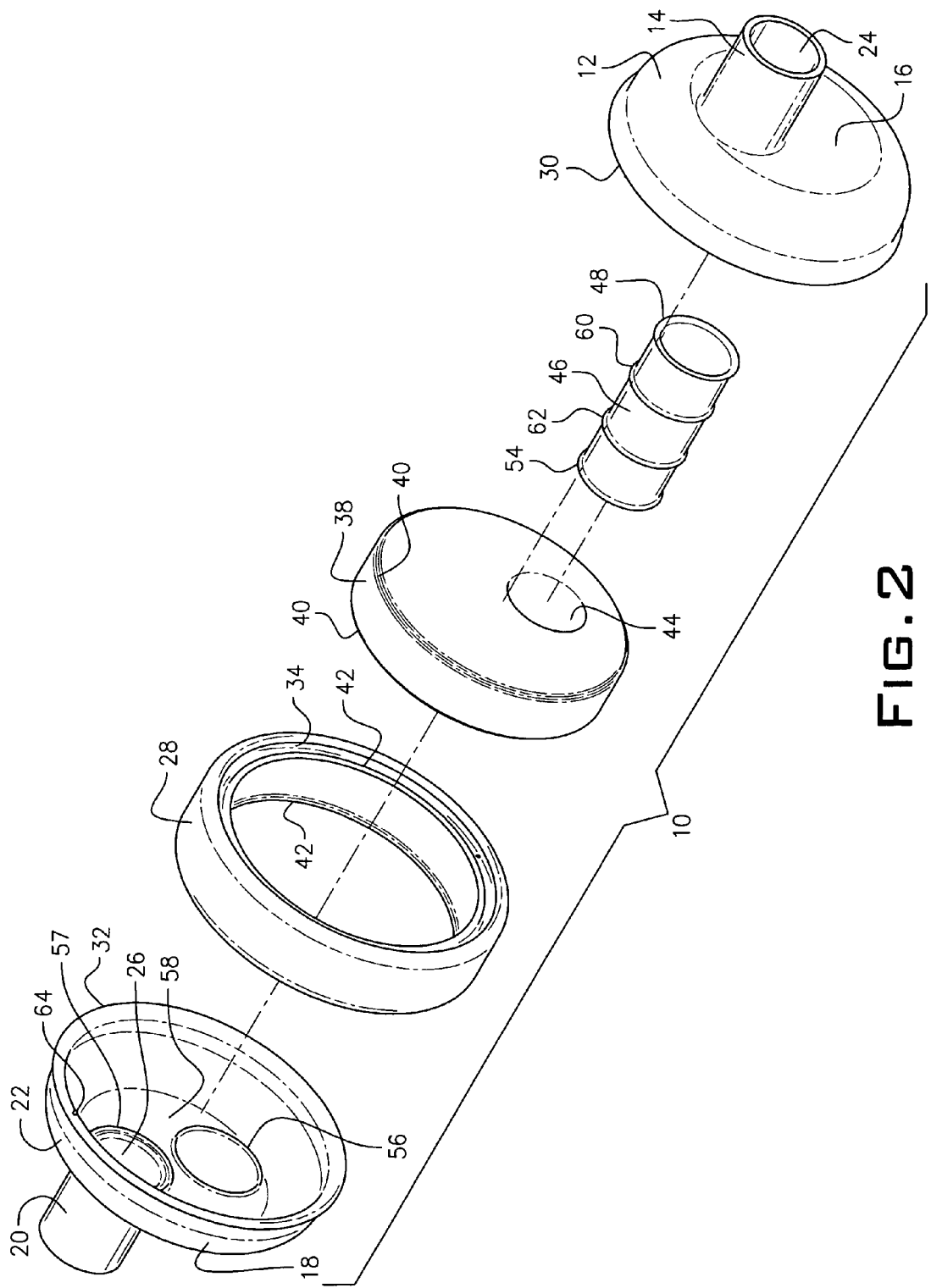
FIG. 2 is a left side exploded view showing the contents of the apparatus shown in FIG. 1.

Referring to FIG. 2, the first housing 12 and second housing 18 each have an annular interior lip 30 and 32 respectively. Rotatable middle housing 28 has a groove 34 on an outer edge of a first side which slides over lip 30 on first housing 12. Likewise, housing 28 has a groove 36 on an outer edge of a second side which slides over lip 32 on second housing 18. A heat-moisture exchange material 38 (HMEM) is mounted within middle housing 28. An exterior groove 40, on each side of HMEM 38, engages a rim 42 on each side of middle cylindrical housing 28 to hold the HMEM in a fixed position within middle housing 28.

Figure 3:
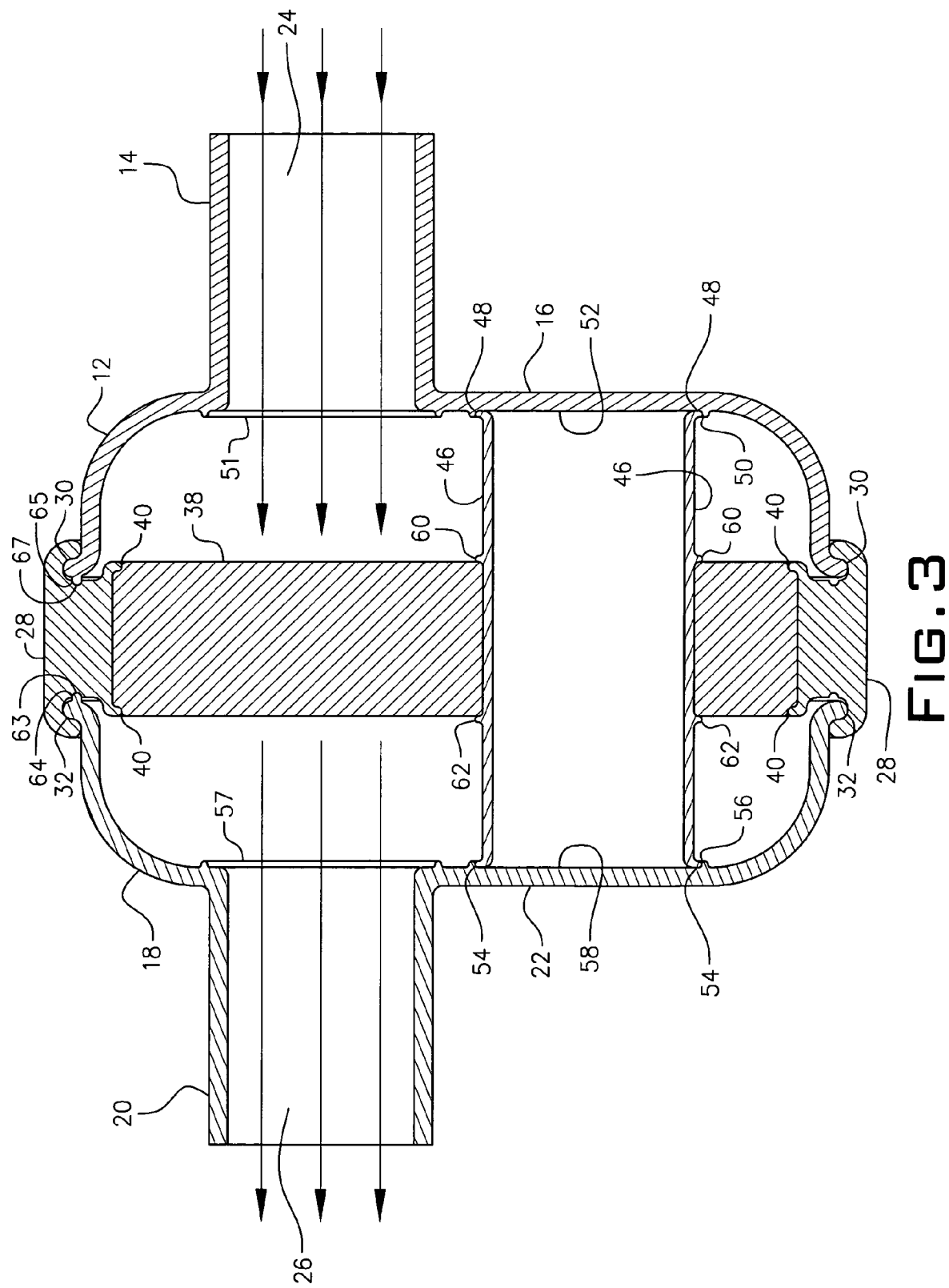
FIG. 3 is a sectional view along lines 3—3 of FIG. 1 showing a second rotatable position of the middle housing.
Figure 4:
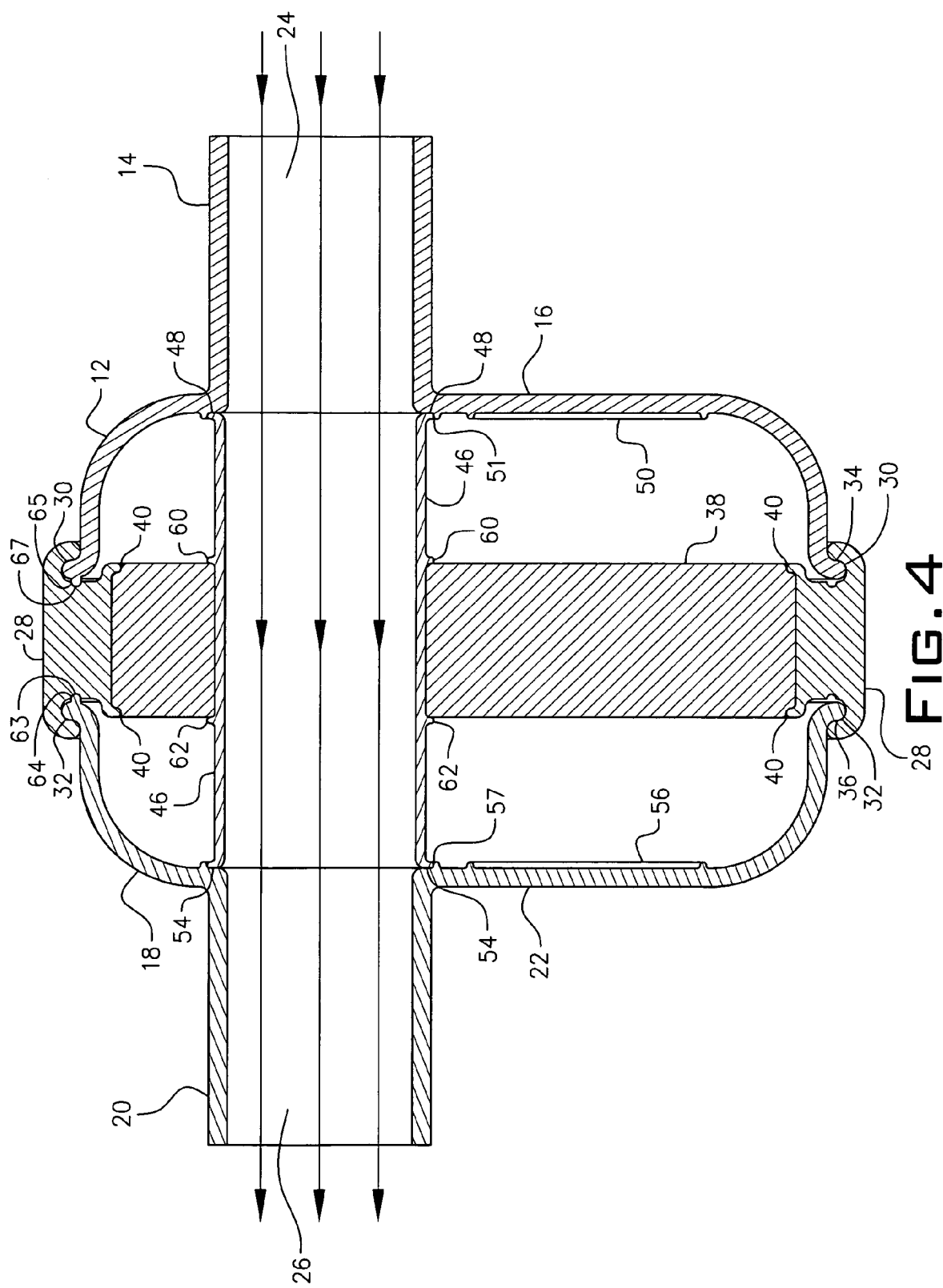
FIG. 4 is a sectional view showing a first rotatable position of the middle housing.
Figure 5:
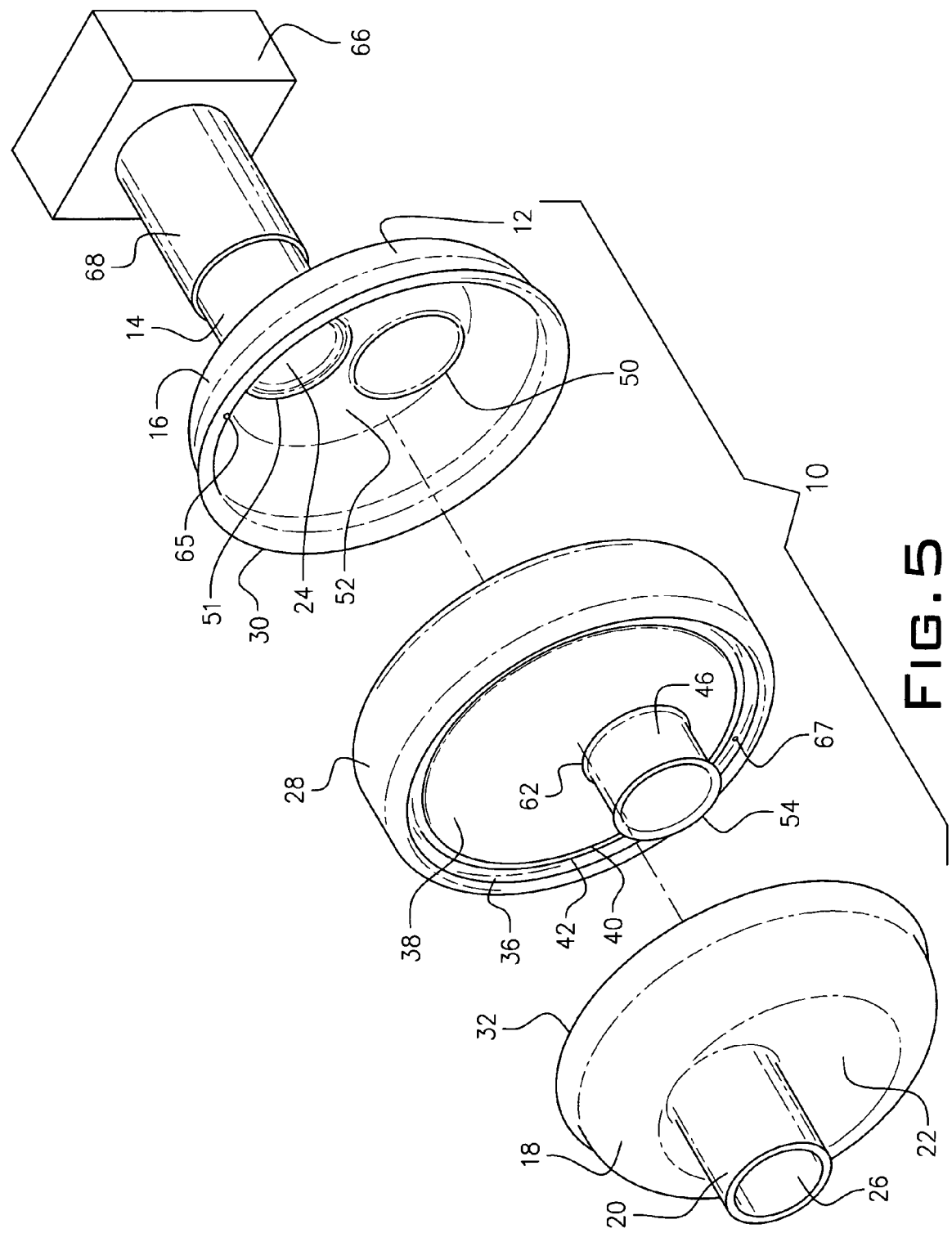
FIG. 5 is an exploded view of the right side of the apparatus connected to an aerosol generator.

The HMEM 38 has an annular opening 44 in which a tube 46 is fixedly mounted. Rim 48 rotates within a groove 50 in the interior wall 52 of housing 12. Rim 54 rotates within a groove 56 in the interior wall 58 of housing 18 in a second rotatable position. See FIG. 3. Rims 60 and 62 on tube 46 fit on each side of annular opening 44 in the HMEM. By turning middle housing 28 to a first rotatable position seen in FIG. 4 the tube 46 lines up axially with passageways 24 and 26 and grooves 51 and 57 respectively so there is no obstruction to the flow of air or liquids through the apparatus. When the use of the HMEM is required the apparatus 10 merely needs to have its middle housing 28 rotated so that the second rotatable position shown in FIG. 3 is achieved. In this position air and moisture from or to the patient must pass through the HMEM.

The components shown above except for the heat-moisture exchange material 38 are made from a rigid high strength plastic such as polypropylene, polyethylene, polyamide or polycarbonate. The HMEM 38 is obtained from polyurethane foam coated in a sodium chloride solution.

By attaching the heat-moisture exchanger 10 of this invention to a patient ventilation system, the normal continuity of the exchanger circuit is not interrupted, but the modified circuit allows for entry of an aerosolized liquid medication from an aerosol generator 66, such as a nebulizer, merely by turning the housing 28 to axially align all the openings. Tube 68 connects the aerosol generator 66 to conduit 14. In this mode, the absorbent HMEM material 38 is by-passed. The device 10 maintains the continuity of a closed ventilator circuit without interruption of the ventilation circuit to a patient.

A nipple 64 on lip 32 of second housing 18 locks into groove 63 on middle 28. Likewise, nipple 65 on lip 30 of first housing 12 locks into groove 67 on middle housing 28.

Other substantially equivalent elements can be substituted for the elements of the heat-moisture exchanger disclosed herein to produce substantially the same results in substantially the same way.

Having described the invention, what is claimed for Letters Patent follows:

1. A patient heat-moisture exchanger apparatus adapted for use with an aerosol generator, the heat exchanger apparatus comprising:
   a first housing having a first conduit integral with an exterior side, the first conduit having a passageway leading inwardly through the exterior side of the first housing;
   a second housing having a second conduit integral with an exterior side, the second conduit having a passageway leading outwardly through the exterior side of the second housing;
   a cylindrical rotatable middle housing interposed between the first and second housing, the middle housing having a channel on opposed sides engageable with an annular interior rim on the first and second housing respectively;
   a heat-moisture exchange material affixed within the middle housing, the heat-moisture exchange material having an opening there through off-set from a central portion of the middle housing;
   an elongated tube mounted within the opening in the heat-exchange material axially aligned in a first rotatable position with the passageways in the first and second conduits; and
   the elongated tube non-aligned with the passageways in the first and second conduit in a second rotatable position so that the flow of air and moisture must pass through the heat-moisture material to and from the patient.

2. The patient heat-moisture exchanger apparatus according to claim 1, wherein the first conduit connects to an aerosol generator.

3. The patient heat-moisture exchanger apparatus according to claim 2, wherein the aerosol generator is a nebulizer.

4. The patient heat-moisture exchanger apparatus according to claim 1, wherein an interior wall of the first and second housing is spaced apart from the heat-moisture exchanger material.

5. The patient heat-moisture exchanger apparatus according to claim 1, wherein an annular ring on an inside wall of the first and second housing engages opposed ends of the elongated tube when the flow of air and moisture must pass through the heat-moisture exchanger material.

6. The patient heat-moisture exchanger apparatus according to claim 1, wherein an annular groove on an inside edge of the first and second conduit engages opposed ends of the elongated tube when there is unimpeded flow of air and moisture from the first to the second conduit.

7. The patient heat-moisture exchanger apparatus according to claim 1, wherein a nipple on the first and second housing engage a depression on opposite sides of the middle housing when the first and second conduits are axially aligned.

8. The patient heat-moisture exchanger apparatus according to claim 1, wherein the first, second and middle housings are rigid structures made from a high strength polymer.

9. A system for alternatively passing a patient's expired breath through a heat-moisture exchanger material and an axially aligned passageway to permit passage of an aerosolized medicament from an aerosol generator, the system comprising:
   a first housing integrally attached to a first conduit having a passageway through an exterior surface of the first housing;
   a second housing integrally attached to a second conduit having a passageway through an exterior surface of the first housing;
   a cylindrically shaped middle housing rotatably attached at opposed ends to the first and second housings;
   a heat-moisture exchanger material mounted within the middle housing, the heat-moisture exchanger material having an axial bore therethrough, the bore offset from a central portion of the middle housing;
   a central portion of an elongated tube mounted within the bore in the heat-exchanger material with opposed ends of the tube engaging an interior surface groove on the first and second housing; and
   the elongated tube axially aligned in a first rotatable position with the passageways in the first and second conduits and non-aligned in a second rotatable position with the passageways in the first and second conduits so that the flow of air and moisture must pass through the heat-moisture exchanger material to and from the patient.

10. The system according to claim 9, wherein one of the conduits is attached to an aerosol generator and the other to a patient's ventilator system.

11. The system according to claim 10, wherein the aerosol generator is a nebulizer.

12. The system according to claim 9, wherein an interior surface of the first and second housing is spaced apart from the heat-moisture exchanger material.

13. The system according to claim 9, wherein the opposed ends of the middle housing have an annular groove in which a rim from the first and second housing respectively rotate.

14. The system according to claim 9, wherein the elongated tube has a pair of spaced apart ribs in the central portion, each rib juxtaposed to opposite exterior sides respectively of the heat-moisture exchanger material.

15. A heat-moisture exchanger apparatus interposed in a patient breathing circuit, the apparatus comprising:
   a first housing having an exterior and interior wall with a conduit integrally attached to the exterior wall, the conduit containing a passageway through the exterior wall;
   a second housing having an exterior and interior wall with a conduit integrally attached to the exterior wall, the conduit containing a passageway through the exterior wall;
   a cylindrically shaped middle housing rotatably attached at opposed annular rims to complementary annular rims on the first and second housing respectively;
   a heat-moisture exchanger material mounted within the middle housing, the heat-moisture exchanger material having an axial bore therethrough, the bore offset from a central portion of the middle housing;
   a central portion of an elongated tube mounted within the bore in the heat-exchanger material, opposed ends of the tube engaging the interior surface of the first and second housing respectively;
   the elongated tube axially aligned in a first rotatable position with the first and second conduit passageways and non-aligned in a second rotatable position with the passageways in the first and second conduits so that the flow of air and moisture must pass through the heat-moisture exchanger material to or from a patient's breathing apparatus or to or from a nebulizer connected to the heat-moisture exchanger apparatus.

* * * * *